United States Patent [19]

Yeung et al.

[11] Patent Number: 5,271,402

[45] Date of Patent: Dec. 21, 1993

[54] TURBINE DRIVE MECHANISM FOR STEERING ULTRASOUND SIGNALS

[75] Inventors: King-Wah W. Yeung, Cupertino; J. Fleming Dias, Palo Alto, both of Calif.

[73] Assignee: Hewlett-Packard Company, Palo Alto, Calif.

[21] Appl. No.: 892,451

[22] Filed: Jun. 2, 1992

[51] Int. Cl.⁵ .............................................. A61B 8/12
[52] U.S. Cl. .............................. 128/660.1; 128/662.06
[58] Field of Search ............ 128/660.01, 660.1, 662.03, 128/662.06; 73/622–623

[56] References Cited

U.S. PATENT DOCUMENTS

| | | | |
|---|---|---|---|
| 4,176,662 | 12/1979 | Frazer | 128/662.06 X |
| 4,432,371 | 2/1984 | McAusland | 128/660.1 |
| 4,490,728 | 12/1984 | Vaught et al. | |
| 4,572,201 | 2/1986 | Kondo et al. | |
| 4,748,985 | 6/1988 | Nagasaki | 128/662.03 X |
| 4,779,624 | 10/1988 | Yokoi | 128/660.03 X |
| 4,794,931 | 3/1989 | Yock | |
| 5,000,185 | 3/1991 | Yock | |
| 5,046,503 | 9/1991 | Schneiderman | 128/662.06 X |
| 5,199,437 | 4/1993 | Langberg | 128/662.06 |

FOREIGN PATENT DOCUMENTS 84401959.6 10/1984 European Pat. Off. .

Primary Examiner—Francis Jaworski

[57] ABSTRACT

An ultrasound probe includes an ultrasound emitter and a turbine. In one embodiment, the ultrasound emitter is a reflective surface which reflects ultrasound signals generated by a transmitter. The reflective surface reflects the ultrasound signals so that reflected ultrasound signals exit the ultrasound probe. The turbine is connected to the reflecting means. Fluid flowing through the turbine causes the turbine to rotate the reflecting means so that the reflected ultrasound signals sweep an area surrounding the ultrasound probe.

30 Claims, 9 Drawing Sheets

TURBINE DRIVE MECHANISM FOR STEERING ULTRASOUND SIGNALS

BACKGROUND

The present invention concerns a turbine drive mechanism which is used to steer ultrasound signals generated by an ultrasound probe.

Catheter-based ultrasound probes are increasingly used in various medical applications, for example, in the imaging and diagnosis of vascular disease. Catheter-based ultrasound probes differ in beam configuration. For example, catheter-based ultrasound probes have been developed with a sector (wedge) beam configuration in which ultrasound beams are directed in a forward direction from the tip of the probe. Catheter-based ultrasound probes have been developed with a conical (funnel) beam configuration in which ultrasound beams are directed radially and at an angle forward. Also, catheter-based ultrasound probes have been developed in which ultrasound beams are directed in a 360 degree scan perpendicular to the long axis of the catheter. The catheter based system may scan an area by using a phased array of transducers, or by using a single mechanically rotated transducer. See, for example, Paul G. Yock, Eric L. Johnson and David T. Linker, *Intravascular Ultrasound: Development and Clinical Potential, American Journal of Cardiac Imaging*, Vol. 2, No. 3 (September), 1988, pp. 185-193.

In one prior art ultrasonic apparatus which uses mechanical movement to direct ultrasound beams outward from the apparatus, an ultrasonic transducer is carried by the distal end of a catheter adapted for insertion into a vessel. Either the transducer or another element is rotated and/or translated relative to the catheter to image different portions of the vessel. See U.S. Pat. No. 5,000,185, issued to Paul G. Yock, for METHOD FOR INTRAVASCULAR TWO-DIMENSIONAL ULTRASONOGRAPHY AND RECANALIZATION. In this prior art ultrasonic apparatus, torque for the rotation is provided via a motor connected through a torque cable to either the ultrasonic transducer or a reflective surface. This eliminates the bulk which results from inclusion of a phased array of piezoelectric transducers. The limited flexibility of a torque cable, however, restricts the range of uses of the ultrasonic apparatus.

SUMMARY OF THE INVENTION

In accordance with the preferred embodiment of the present invention, an ultrasound probe is presented. The ultrasound probe includes an emitter of ultrasound signals and a turbine. In one embodiment, the emitter includes a reflective surface which reflects ultrasound signals generated by a transducer. The reflective surface reflects the ultrasound signals so that reflected ultrasound signals exit the ultrasound probe. The turbine is connected to the reflecting means. Fluid flowing through the turbine causes the turbine to rotate the reflecting means so that the reflected ultrasound signals sweep an area surrounding the ultrasound probe.

Different embodiments of the present invention provide the fluid to the turbine in various ways. For example, in a first embodiment of the present invention, the fluid flowing through the turbine is resident within a probed vessel within which the ultrasound probe is situated. The fluid enters the ultrasound probe through holes in a head of the ultrasound probe. This embodiment may not be effective for use in blood vessels without a sufficient fluid flow.

In alternate embodiments of the present invention, the fluid within the ultrasound probe is vibrated to cause the fluid, for example air, to pass through the turbine. For example, the fluid may be vibrated using externally provided fluid transported between the ultrasound probe and an external source via a tube. Alternately, the fluid may be vibrated using a piezoelectric transducer. A ratchet can be used to assure that the turbine is able to turn in only a single direction. Alternately, when the piezoelectric transducer generates standing acoustic waves within the ultrasound probe, there may be no need for using a ratchet for controlling the step size. In this case, use of a directional clutch ensures easy rotation of the turbine in one direction only.

In another embodiment of the present invention, the fluid is transported to the ultrasound probe from an external source. This may be done, for example, using an inflow tube to transport the fluid from the external source to the ultrasound probe, and using an outflow tube to transport the fluid from the ultrasound probe to the external source.

The present invention eliminates the need to attach an inflexible drive cable to an ultrasound probe. Further, the object of the present invention is accomplished without placing a motor drive within the ultrasound probe. Placing a motor drive within the ultrasound probe could result in a bulky and more expensive ultrasound probe. The present invention, however, allows for the construction of a flexible, miniature and low cost ultrasound probe.

DESCRIPTION OF THE PREFERRED EMBODIMENT

Figure 1:
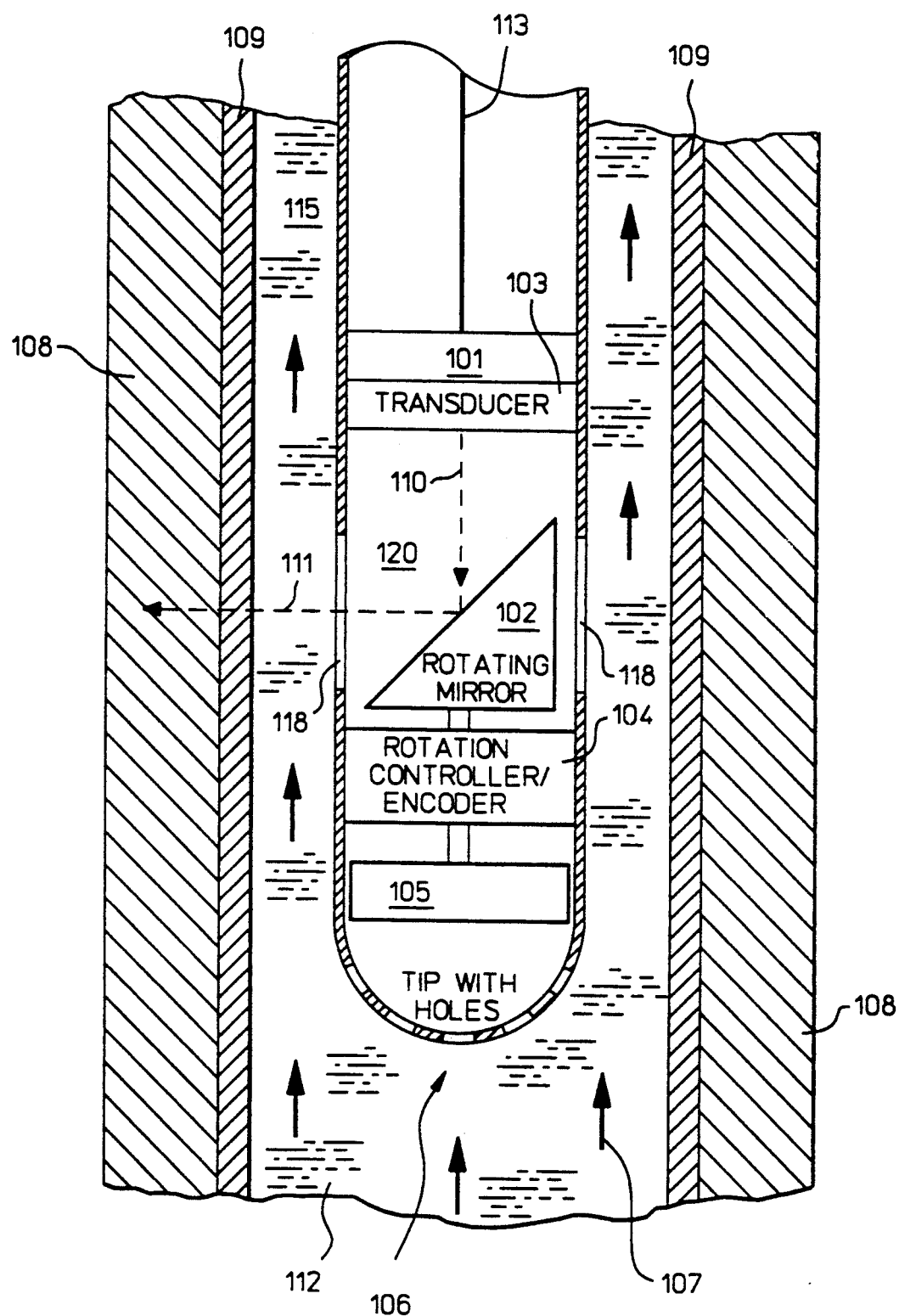
FIG. 1 shows an ultrasound probe with a rotating acoustic reflector (mirror) connected to a turbine driven by moving fluid in accordance with a first preferred embodiment of the present invention.

FIG. 1 shows, within a vessel 115, an ultrasound probe 101, residing within a catheter, in accordance with a first preferred embodiment of the present invention. Ultrasound probe 101 includes a transducer 103 which generates ultrasound signals from electrical signals carried to ultrasound probe 101 through wire cable 113. Ultrasound signals from transducer 103, traveling in a direction 110, are reflected by a rotating acoustic reflector (mirror) 102, for example, in a radial direction 111 from ultrasound probe 101.

The ultrasound signals pass through an acoustically transparent window 118 of ultrasound probe 101 and the catheter which encloses ultrasound probe 101. The ultrasound signals are partially reflected by vessel walls 109 and tissue 108. The reflected portion of the ultrasound signals propagate back to rotating mirror 102 and thereafter to transducer 103. Transducer 103 generates electrical signals which are carried by wire cable 113 and which may be used to image a cross section of vessel 115. A coupling fluid 120 is sealed inside probe 101 to enable transmission of ultrasound signals between transducer 103 and transparent window 118.

The use of a transducer within an ultrasound probe for acoustic imaging of a vessel has been described, see for example U.S. Pat. No. 5,000,185 cited above. From prior art systems it is understood that transducer 103 may be, for example, a piezoelectric ceramic resonator with a suitable backing which absorbs acoustic pulse signals which emanate from the piezoelectric ceramic resonator in a direction other than direction 110. Alternately, transducer 103 may be made by various other methods known in the art.

In the preferred embodiment of the present invention, rotating mirror 102 is connected to a turbine 105. Turbine 105 is located near a permeated tip 106 of ultrasound probe 101. Moving fluid 112 within vessel 115, flowing in a direction 107, flows through holes in permeated tip 106 and drives turbine 105. Turbine 105 may be, for example, a multiple blade turbine constructed of molded plastic. When it is desirable to miniaturize ultrasound probe 101, a turbine may be constructed using electroforming, extrusion, or other micromachining techniques known in the art.

A rotation controller/encoder 104 stores any excess energy produced by turbine 105, controls rotation of rotating mirror 102, and encodes the angle of rotating mirror 102 into electrical signals which are carried by wire cable 113. The electrical signals are used to time ultrasonic bursts generated by transducer 103.

The design of rotation controller/encoder 104 may be simplified by placing a thin highly acoustically reflective strip as a marker on acoustically transparent window 118 of ultrasound probe 101. The acoustic reflection from the acoustically reflective strip is encoded within the electrical signals generated by transducer 103, and transported by wire cable 113. The electrical signal resulting from the acoustic reflections from the reflective strip serves as a marker, indicating when rotating mirror 102 reflects ultrasound bursts through the portion of acoustically transparent window 118 where the acoustic reflective strip resides. The resulting mark within the electrical signal is used to calculate the angular speed from the frequency of rotation of rotating mirror 102. From this the orientation of rotating mirror 102 within ultrasound probe 101 with respect to time is simply derived, as is clearly understood by those skilled in the art.

The design of ultrasound probe 101 is perfectly adequate for applications where there is sufficient fluid flow to drive turbine 105. For example, a vessel with a fluid flow of 50 centimeters per second presents an adequate environment for the use of ultrasound probe 101 with a turbine of three millimeters in diameter. However, for applications where fluid flow is minimal, as in the case of some blood vessels, an alternate embodiment of the present invention should be used.

Figure 2:
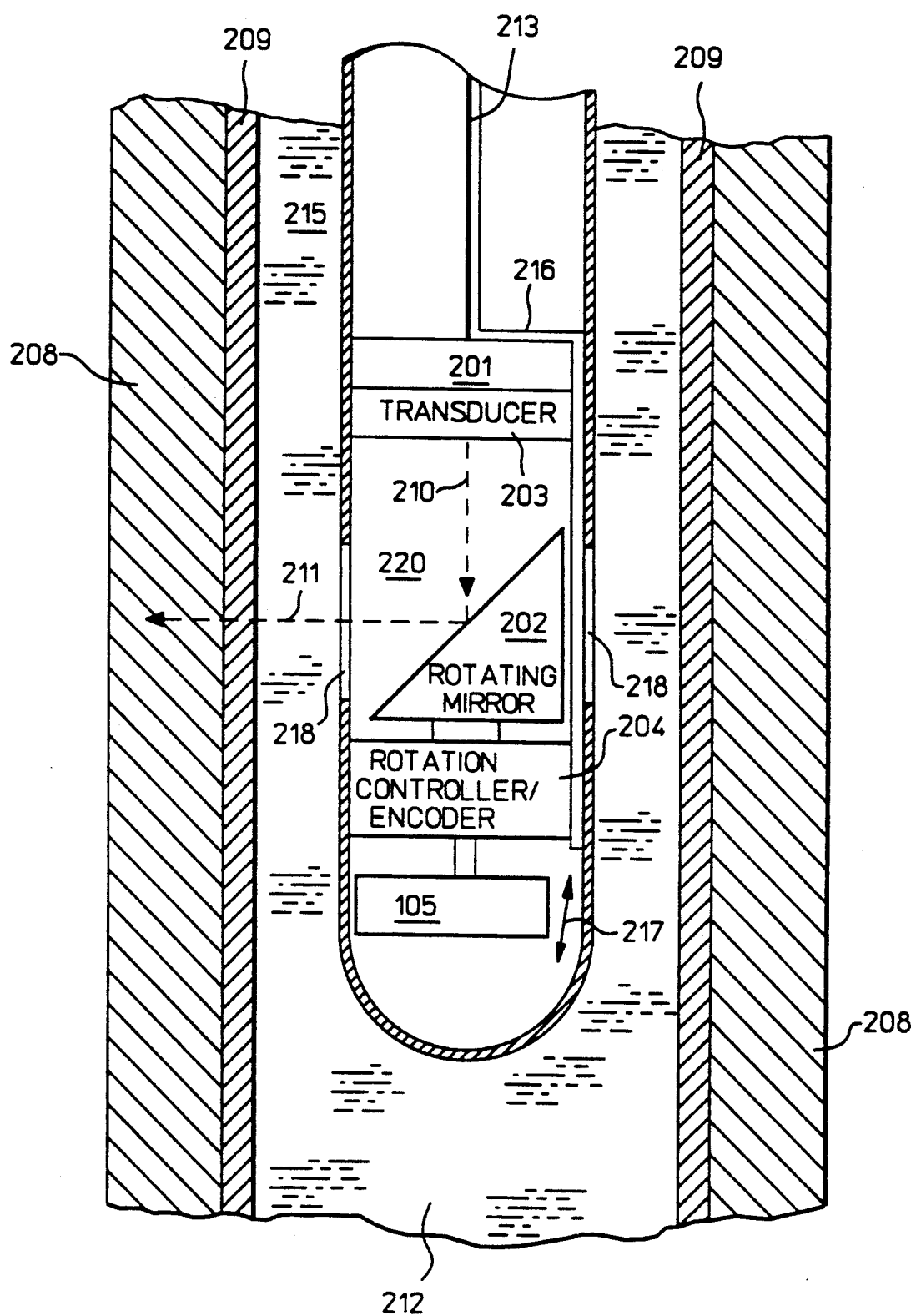
FIG. 2 shows an ultrasound probe with a rotating acoustic reflector (mirror) connected to a turbine driven by vibrating fluid provided by a tube in accordance with a second preferred embodiment of the present invention.

FIG. 2 shows, within a vessel 215, an ultrasound probe 201, residing within a catheter, in accordance with a second preferred embodiment of the present invention. Ultrasound probe 201 includes a transducer 203 which generates ultrasound signals from electrical signals carried to ultrasound probe 201 through wire cable 213. Ultrasound signals from transducer 203, traveling in a direction 210, are reflected by a rotating acoustic reflector (mirror) 202, for example, in a radial direction 211 from ultrasound probe 201.

The ultrasound signals pass through an acoustically transparent window 218 of ultrasound probe 201. The ultrasound signals are partially reflected by vessel walls 209 and tissue 208. The reflected portion of the ultrasound signals are reflected back to transducer 203 by rotating mirror 202. Transducer 203 generates electrical signals which are carried by wire cable 213 and which may be used to image a cross section of vessel 215. A coupling fluid 22 is sealed inside probe 201 to enable transmission of ultrasound signals between transducer 203 and transparent window 218.

Rotating mirror 202 is connected to a turbine 205. Turbine 205 is driven by vibrating fluid, for example air, supplied from a tube 216. The fluid vibrations are represented by arrows 217. Turbine 205 is excited by the vibrations of the fluid but is enabled to turn in only one direction. For example, a mechanical ratchet within a rotation controller/encoder 204, permits turbine 205 to step with a small fixed angle each time the pressure of the fluid is high enough to drive turbine 205 to rotate in the enabled direction. As a result, the stepping frequency of turbine 205 equals the vibration frequency of the driving fluid. The angle of rotation of rotating mirror 202 can be obtained by counting the number of elapsed cycles of air vibration after a "home" angle has been detected by a simple encoder within rotation controller/encoder 204. Further, as discussed above, a thin highly acoustically reflective strip can be placed as a marker on acoustically transparent window 218 of ultrasound probe 201. The electrical signal resulting from the acoustic reflections from the reflective strip serves as a marker, indicating when rotating mirror 202 reflects ultrasound bursts through the portion of acoustically transparent window 218 where the acoustic reflective strip resides.

Figure 3:
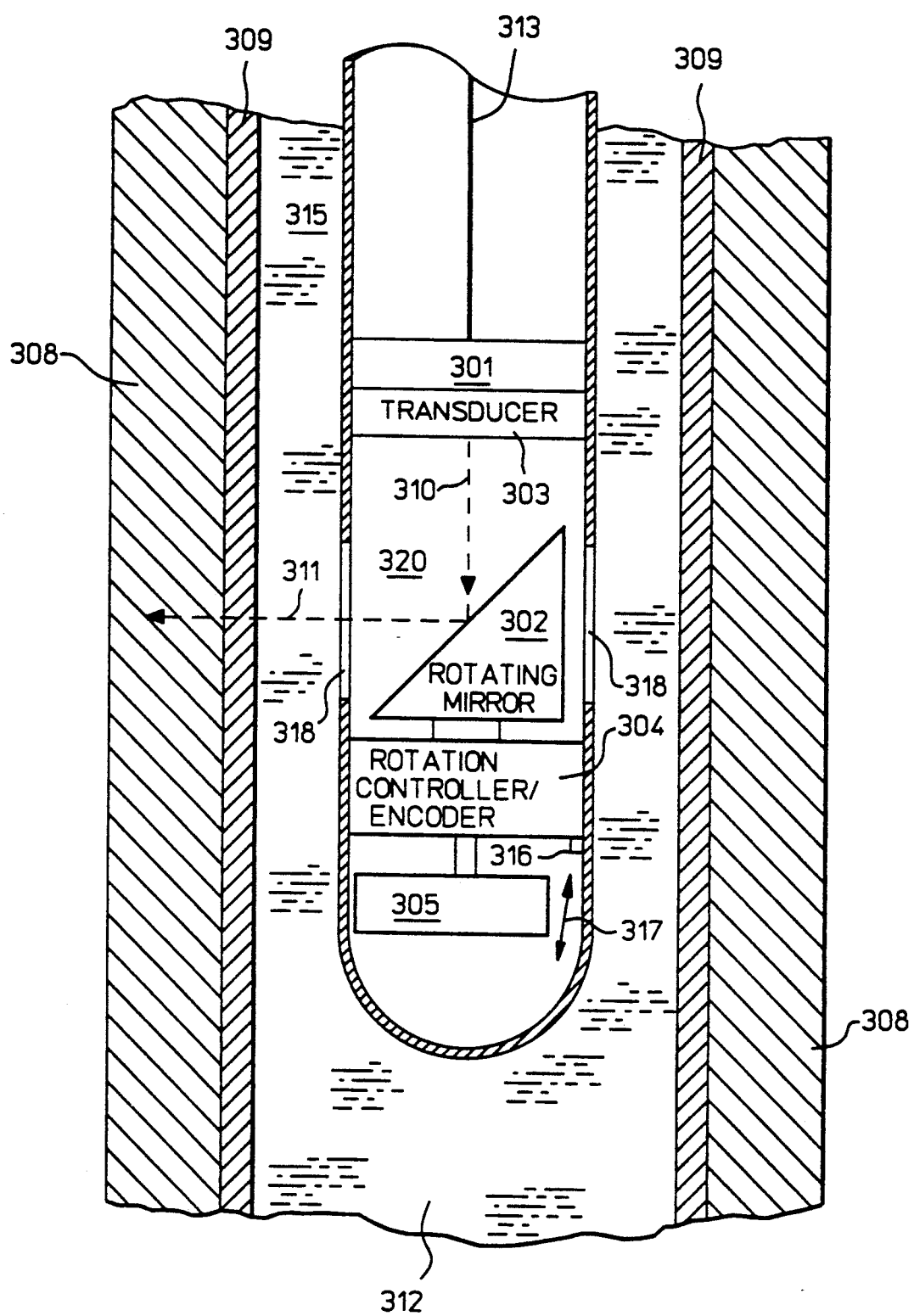
FIG. 3 shows an ultrasound probe with a rotating acoustic reflector (mirror) connected to a turbine driven by fluid vibrated by a stack of piezoelectric transducers in accordance with a third preferred embodiment of the present invention.

FIG. 3 shows, within a vessel 315, an ultrasound probe 301, residing within a catheter, in accordance with a third preferred embodiment of the present invention. Ultrasound probe 301 includes a transducer 303 which generates ultrasound signals from electrical signals carried to ultrasound probe 301 through wire cable 313. Ultrasound signals from transducer 303, traveling in a direction 310, are reflected by a rotating acoustic reflector (mirror) 302, for example, in a radial direction 311 from ultrasound probe 301.

The ultrasound signals pass through an acoustically transparent window 318 of ultrasound probe 301. The ultrasound signals are partially reflected by vessel walls 309 and tissue 308. The reflected portion of the ultrasound signals are reflected back to transducer 303 by rotating mirror 302. Transducer 303 generates electrical signals which are carried by wire cable 313 and which may be used to image a cross section of vessel 315. A coupling fluid 320 is sealed inside probe 301 to enable transmission of ultrasound signals between transducer 303 and transparent window 318.

Rotating mirror 302 is connected to a turbine 305. Turbine 305 is driven by vibrating fluid, for example air. A stack of piezoelectric transducers 316 enclosed in a chamber is used to produce vibrations. The fluid vibrations are represented by arrows 317. Turbine 305 is excited by the vibrating fluid but is enabled to turn in only one direction. For example, a mechanical ratchet within a rotation controller/encoder 304, permits turbine 305 to step with a small fixed angle each time the pressure of the fluid is high enough to drive turbine 305 to rotate in the enabled direction. As a result, the stepping frequency of turbine 305 equals the vibration frequency of the driving fluid.

Piezoelectric transducer 316 is powered and controlled by electrical signals transported to ultrasound probe 301 through wire cable 313. The angle of rotation of rotating mirror 302 can be obtained by counting the number of elapsed cycles of air vibration after a "home" angle has been detected by a simple encoder within rotation controller/encoder 304. Further, as discussed above, a thin highly acoustically reflective strip can be placed as a marker on acoustically transparent window 318. The electrical signal resulting from the acoustic reflections from the reflective strip serves as a marker, indicating when rotating mirror 302 reflects ultrasound bursts through the portion of acoustically transparent window 318 where the acoustic reflective strip resides.

The use of piezoelectric transducer 316 allows for the generation of a higher vibration frequency than the design shown in FIG. 2, allowing for a faster stepping speed. Further, if the blades of turbine 305 are designed to match the wave length of standing acoustic waves generated by piezoelectric transducer 316, precise stepping of turbine 305 can be accomplished without utilizing a mechanical ratchet within rotation controller/encoder 304. Specifically, the turbine enclosure is filled with a fluid capable of supporting a standing wave. The spacing of the turbine blades are matched to the wavelength of the standing wave so that the blades will advance by one wavelength distance during each period of the standing wave, without using a mechanical ratchet to control the step size.

Figure 4:
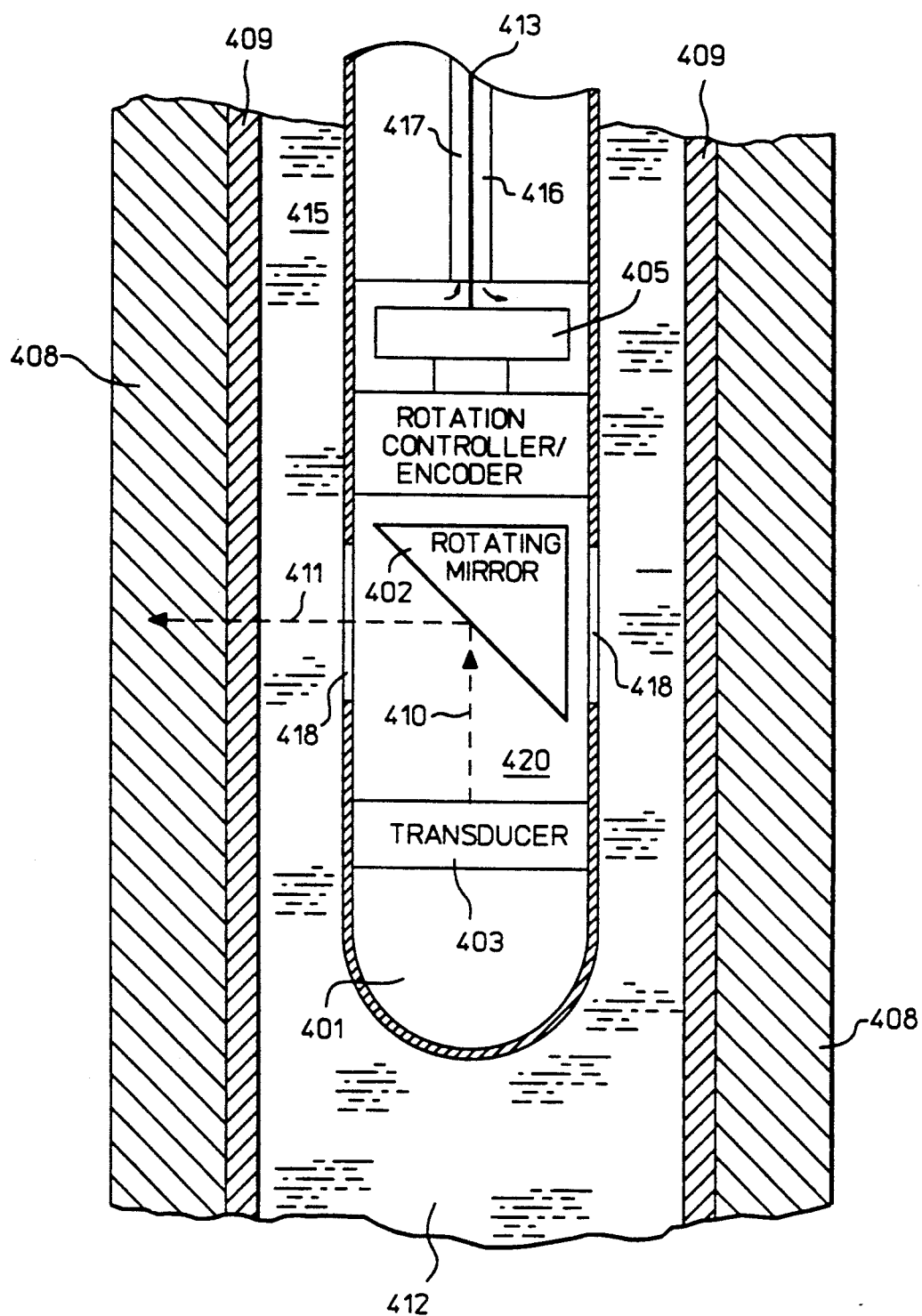
FIG. 4 shows an ultrasound probe with a rotating acoustic reflector (mirror) connected to a turbine driven by fluid provided by a tube in accordance with a fourth preferred embodiment of the present invention.

FIG. 4 shows, within a vessel 415, an ultrasound probe 401, residing within a catheter, in accordance with a fourth preferred embodiment of the present invention. Ultrasound probe 401 includes a transducer 403 which generates ultrasound signals from electrical signals carried to ultrasound probe 401 through wire cable 413. Ultrasound signals from transducer 403, traveling in a direction 410, are reflected by a rotating acoustic reflector (mirror) 402, for example, in a radial direction 411 from ultrasound probe 401.

The ultrasound signals pass through an acoustically transparent window 418 of ultrasound probe 401. The ultrasound signals are partially reflected by vessel walls 409 and tissue 408. The reflected portion of the ultrasound signals are reflected back to transducer 403 by rotating mirror 402. Transducer 403 generates electrical signals which are carried by wire cable 413 and which may be used to image a cross section of vessel 415. A coupling fluid 420 is sealed inside probe 401 to enable transmission of ultrasound signals between transducer 403 and transparent window 418.

Rotating mirror 402 is connected to a turbine 405. Turbine 405 is driven by fluid, for example air, supplied from an inflow tube 416. The fluid exits ultrasound probe 401 through an outflow tube 417. A continuous fluid flow will cause turbine 405 to rotate smoothly, without stepping. Because of the possibility of a malfunction resulting in the fluid escaping from the catheter, it may be desirable to drive turbine 405 with a fluid other than air, for example a saline solution. Also, pulsating fluid flow can be used to step the rotation of turbine 405. A rotation controller/encoder 404 stores any excess energy produced by turbine 405, controls rotation of rotating mirror 402, and encodes the angle of rotating mirror 402 into electrical signals which are carried by wire cable 413.

The design of the rotation controller/encoder 404 may be simplified by placing a thin highly acoustically reflective strip as a marker on acoustically transparent window 418. The acoustic reflection from the acoustically reflective strip is encoded within the electrical signals generated by transducer 403, transported by wire cable 413. The electrical signal resulting from the acoustic reflections from the reflective strip serves as a marker, indicating when rotating mirror 402 reflects ultrasound bursts through the portion of acoustically transparent window 418 where the acoustic reflective strip resides. The resulting mark within the electrical signal is used to calculate the frequency of rotation and the angular speed of rotating mirror 402. The flow of fluid through inflow tube 416 and outflow tube 417 may then be varied until turbine 405 rotates at the desired speed.

Figure 5:
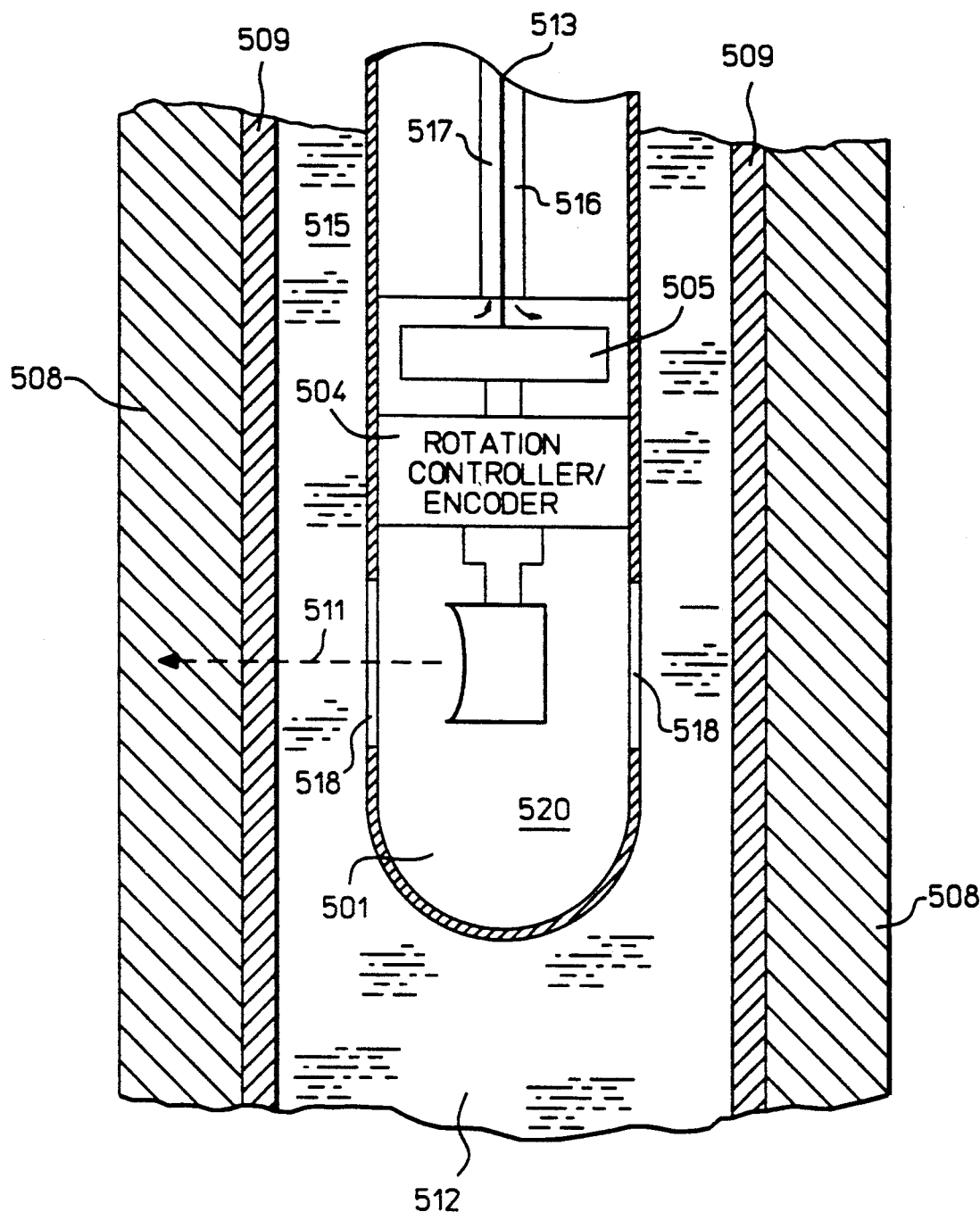
FIG. 5 shows an ultrasound probe with a rotating transducer element connected to a turbine driven by fluid provided by a tube in accordance with a fifth preferred embodiment of the present invention.

FIG. 5 shows, within a vessel 515, an ultrasound probe 501, residing within a catheter, in accordance with a fifth preferred embodiment of the present invention. Ultrasound probe 501 includes a rotating transducer 503 which generates ultrasound signals from electrical signals carried to ultrasound probe 501 through wire cable 513. Ultrasound signals from rotating transducer 503 travel, for example, in a radial direction 511 from ultrasound probe 501.

The ultrasound signals pass through an acoustically transparent window 518 of ultrasound probe 501. The ultrasound signals are partially reflected by vessel walls 509 and tissue 508. The reflected portion of the ultrasound signals are reflected back to rotating transducer 503. Rotating transducer 503 generates electrical signals which are carried by wire cable 513 and which may be used to image a cross section of vessel 515. A coupling fluid 520 is sealed inside probe 501 to enable transmission of ultrasound signals between transducer 503 and transparent window 518.

Rotating transducer 503 is connected to a turbine 505. Turbine 505 is driven by fluid, for example air, supplied from an inflow tube 516. The fluid exits ultrasound probe 501 through an outflow tube 517. A continuous fluid flow will cause turbine 505 to rotate smoothly, without stepping. Because of the possibility of a malfunction resulting in the fluid escaping from the catheter, it may be desirable to drive turbine 505 with a fluid other than air, for example a saline solution. Also, pulsating fluid flow can be used to step the rotation of turbine 505. A rotation controller/encoder 504 stores any excess energy produced by turbine 505, controls rotation of rotating transducer 503, and encodes the angle of rotating transducer 503 into electrical signals which are carried by wire cable 513.

The design of the rotation controller/encoder 504 ma be simplified by placing a thin highly acoustically reflective strip as a marker on acoustically transparent window 518. The acoustic reflection from the acoustically reflective strip is encoded within the electrical signals generated by rotating transducer 503, transported by wire cable 513. The electrical signal resulting from the acoustic reflections from the reflective strip serves as a marker, indicating when rotating transducer 503 transmits ultrasound bursts through the portion of acoustically transparent window 518 where the acoustic reflective strip resides. The resulting mark within the electrical signal is used to calculate the frequency of rotation and the angular speed of rotating transducer 503. The flow of fluid through inflow tube 516 and outflow tube 517 may then be varied until turbine 505 rotates at the desired angular speed.

Figure 6:
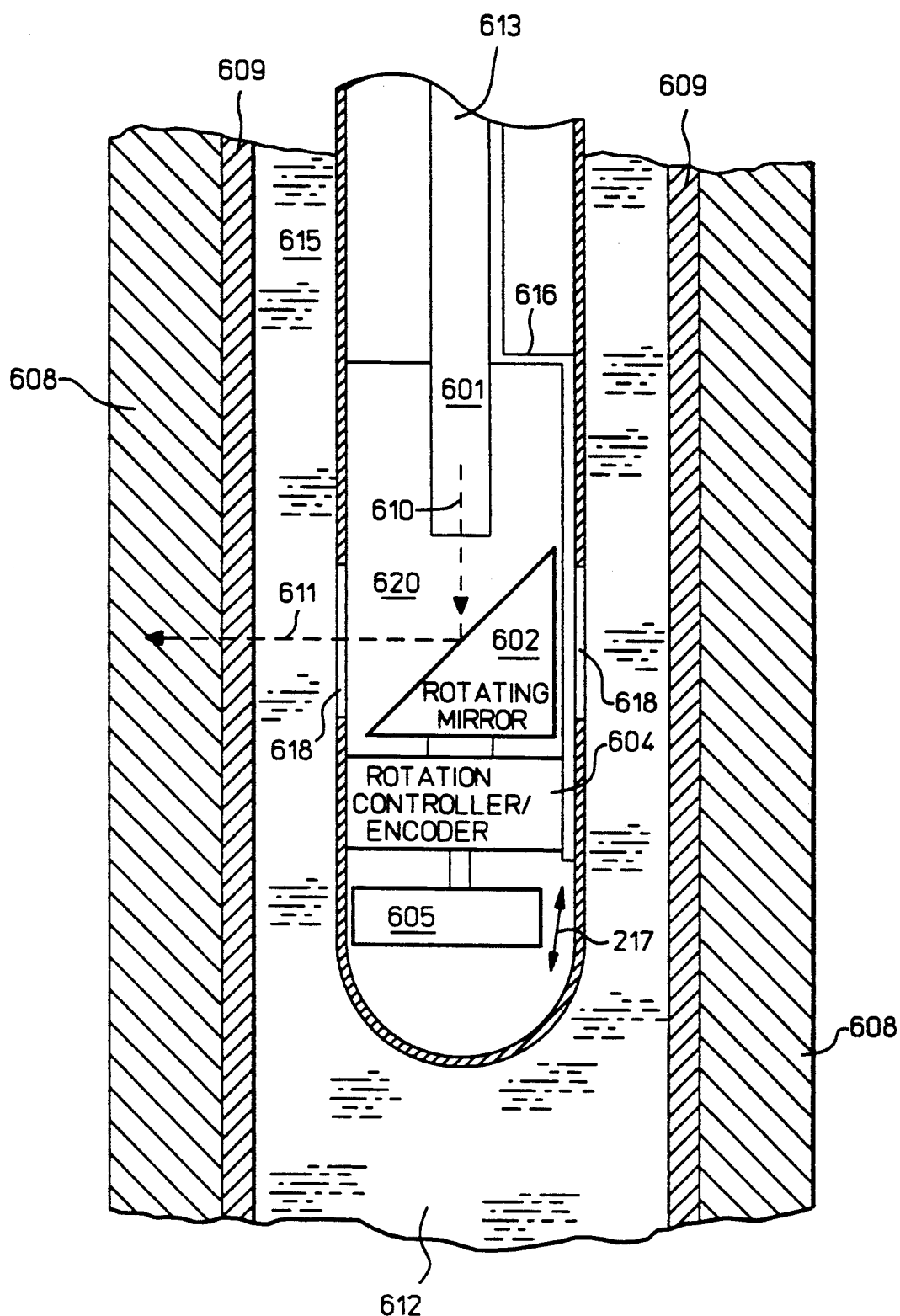
FIG. 6 shows an ultrasound probe with an acoustic waveguide and a rotating acoustic reflector (mirror) connected to a turbine driven by vibration fluid provided by a tube in accordance with a sixth preferred embodiment of the present invention.

FIG. 6 shows, within a vessel 615, an ultrasound probe 601, residing within a catheter, in accordance with a sixth preferred embodiment of the present invention. Ultrasound probe 601 receives ultrasound signals via an acoustic waveguide 613. The ultrasound signals, when received by ultrasound probe 601, travel in a direction 610 and are reflected by a rotating acoustic reflector (mirror) 602, for example, in a radial direction 611 from ultrasound probe 601.

The ultrasound signals pass through an acoustically transparent window 618 of ultrasound probe 601. The ultrasound signals are partially reflected by vessel walls 609 and tissue 608. The reflected portion of the ultrasound signals are reflected back to acoustic waveguide 613 by rotating mirror 602. Acoustic waveguide 613 returns the ultrasound signals to a transducer at the other end of waveguide 613. The electrical signals from the transducer may be used to image a cross section of vessel 615. A coupling fluid 620 is sealed inside probe 601 to enable transmission of ultrasound signals between waveguide 613 and transparent window 618.

Rotating mirror 602 is connected to a turbine 605. Turbine 605 is driven by vibrating fluid, for example air, supplied from a tube 616. The fluid vibrations are represented by arrows 617. Turbine 605 is excited by the vibrations of the fluid but is enabled to turn in only on direction. For example, a mechanical ratchet within a rotation controller/encoder 604, permits turbine 605 to step with a small fixed angle each time the pressure of the fluid is high enough to drive turbine 605 to rotate in the enabled direction. As a result, the stepping frequency of turbine 605 equals the vibration frequency of the driving fluid. The angle of rotation of rotating mirror 602 can be obtained by counting the number of elapsed cycles of air vibration after a "home" angle has been detected by a simple encoder within rotation controller/encoder 604. Further, as discussed above, a thin highly acoustically reflective strip can be placed as a marker on acoustically transparent window 618 of ultrasound probe 601. The electrical signal resulting from the acoustic reflections from the reflective strip serves as a marker, indicating when rotating mirror 602 reflects ultrasound bursts through the portion of acoustically transparent window 618 where the acoustic reflective strip resides.

Figure 7:
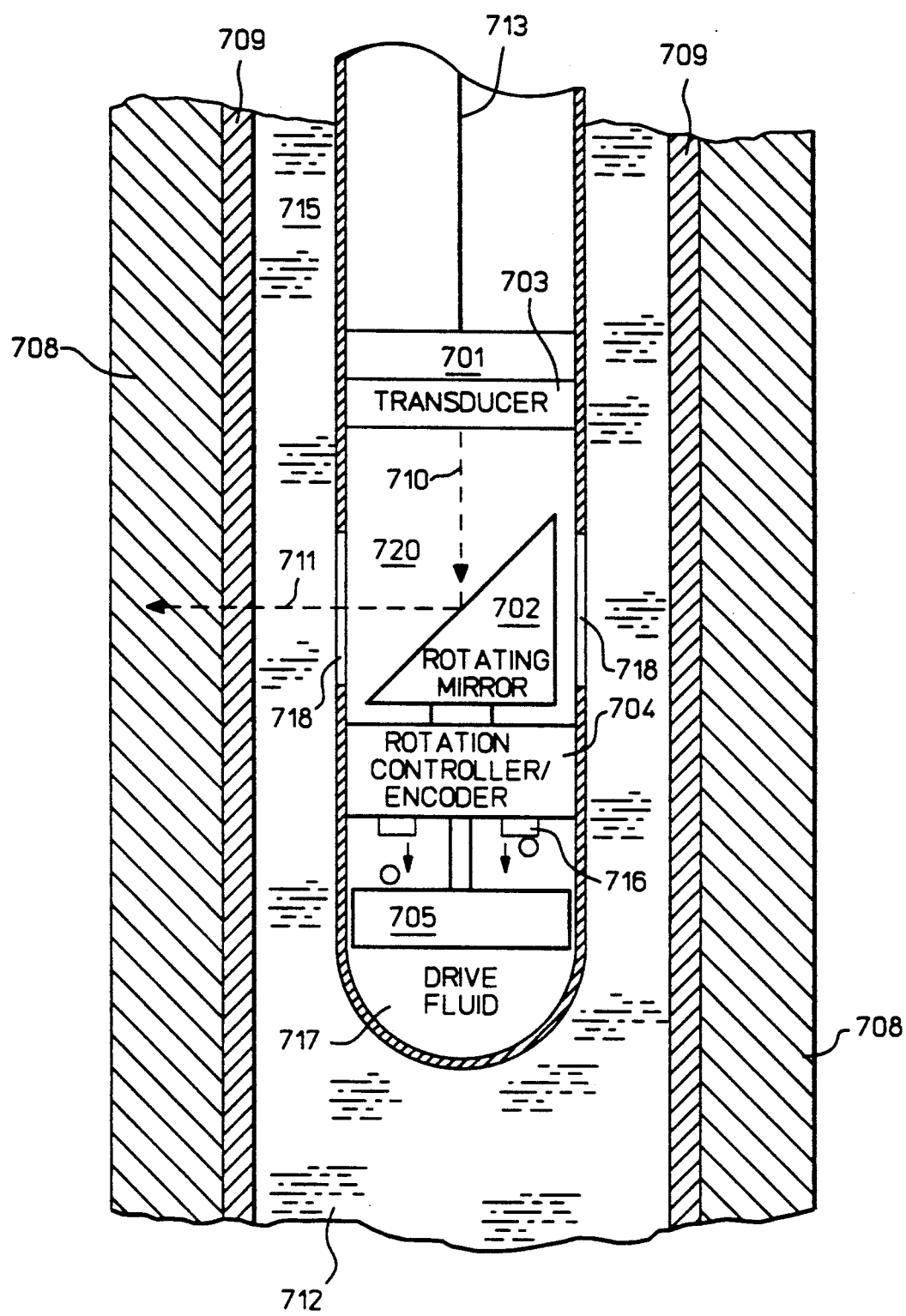
FIG. 7 shows an ultrasound probe with a rotating acoustic reflector (mirror) connected to a turbine driven by vapor bubbles generated from electrical heaters in accordance with a seventh preferred embodiment of the present invention.

FIG. 7 shows, within a vessel 715, an ultrasound probe 701, residing within a catheter, in accordance with a seventh preferred embodiment of the present invention. Ultrasound probe 701 includes a transducer 703 which generates ultrasound signals from electrical signals carried to ultrasound probe 701 through wire cable 713. Ultrasound signals from transducer 703, traveling in a direction 710, are reflected by a rotating acoustic reflector (mirror) 702, for example, in a radial direction 711 from ultrasound probe 701.

The ultrasound signals pass through an acoustically transparent window 718 of ultrasound probe 701. The ultrasound signals are partially reflected by vessel walls 709 and tissue 708. The reflected portion of the ultrasound signals are reflected back to transducer 703 by rotating mirror 702. Transducer 703 generates electrical signals which are carried by wire cable 713 and which may be used to image a cross section of vessel 715. A coupling fluid 720 is sealed inside probe 701 to enable transmission of ultrasound signals between transducer 703 and transparent window 718.

Rotating mirror 702 is connected to a turbine 705. Turbine 705 is driven by vapor bubbles generated from electrical heaters 716. The explosive formation of a vapor bubble within the drive fluid 717 due to the application of an electrical pulse to a resistor (electrical heater) within drive fluid 717 transfers kinetic energy to the turbine. The electrical pulse very quickly heats the resistor to near the superheat limit of the drive fluid 717. Such a formation of vapor bubbles is discussed in U.S. Pat. No. 4,490,728 issued to Vaught et al. on Dec. 25, 1984 for a *Thermal Ink Jet Printer*, the subject matter of which patent is hereby incorporated by reference.

Electrical heater 716 is powered and controlled by electrical signals transported to ultrasound probe 701 through wire cable 713. The use of electrical heater 716 allows for a faster stepping speed than the design shown in FIG. 2. The angle of rotation of rotating mirror 702 can be obtained by counting the number of electrical pulses after a "home" angle has been detected by a simple encoder within rotation controller/encoder 704. Further, as discussed above, a thin highly acoustically reflective strip can be placed as a marker on acoustically transparent window 718. The electrical signal resulting from the acoustic reflections from the reflective strip serves as a marker, indicating when rotating mirror 702 reflects ultrasound bursts through the portion of acoustically transparent window 718 where the acoustic reflective strip resides.

Figure 8:
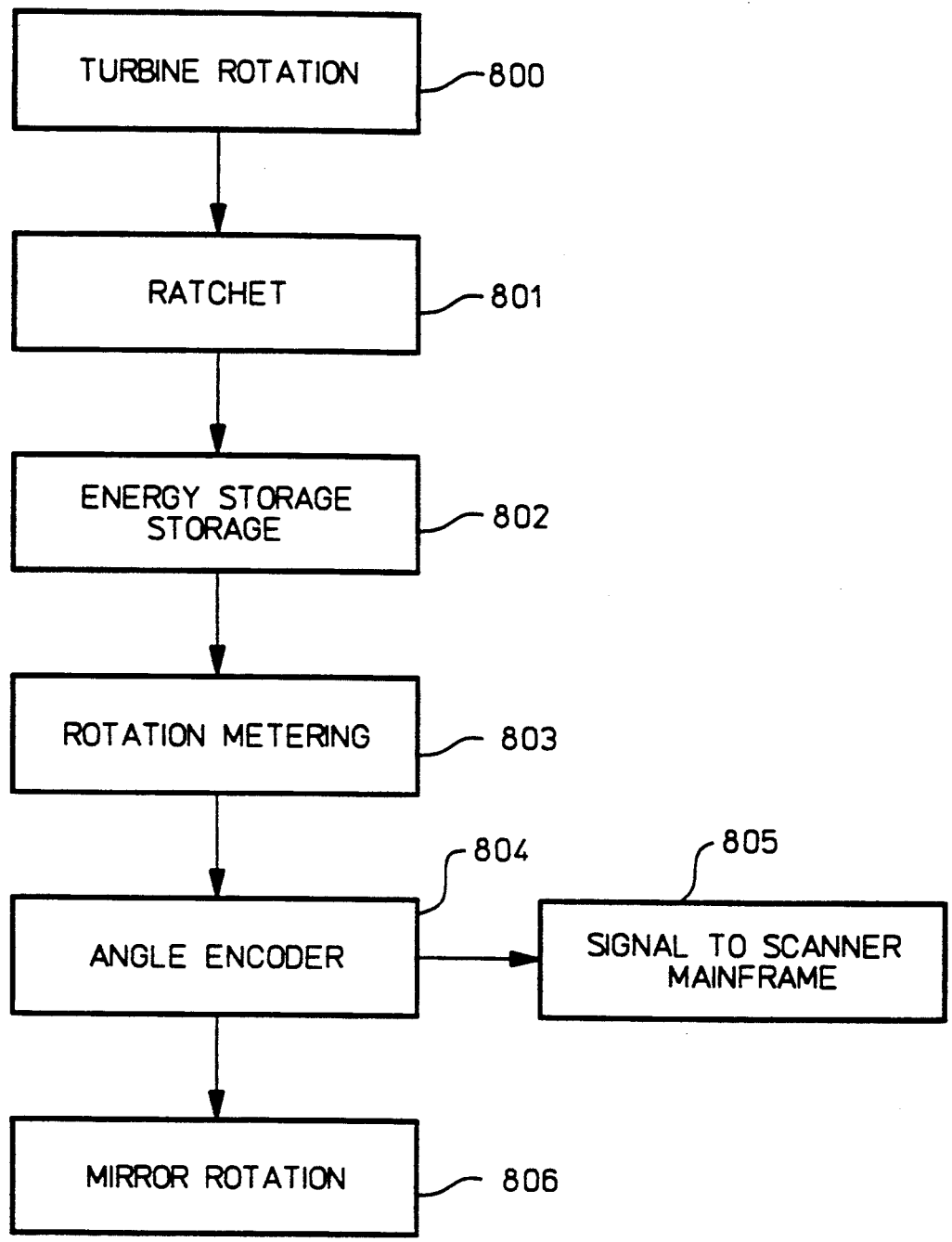
FIG. 8 shows a simplified block diagram of a rotation controller/encoder in accordance with a preferred embodiment of the present invention.
Figure 9:
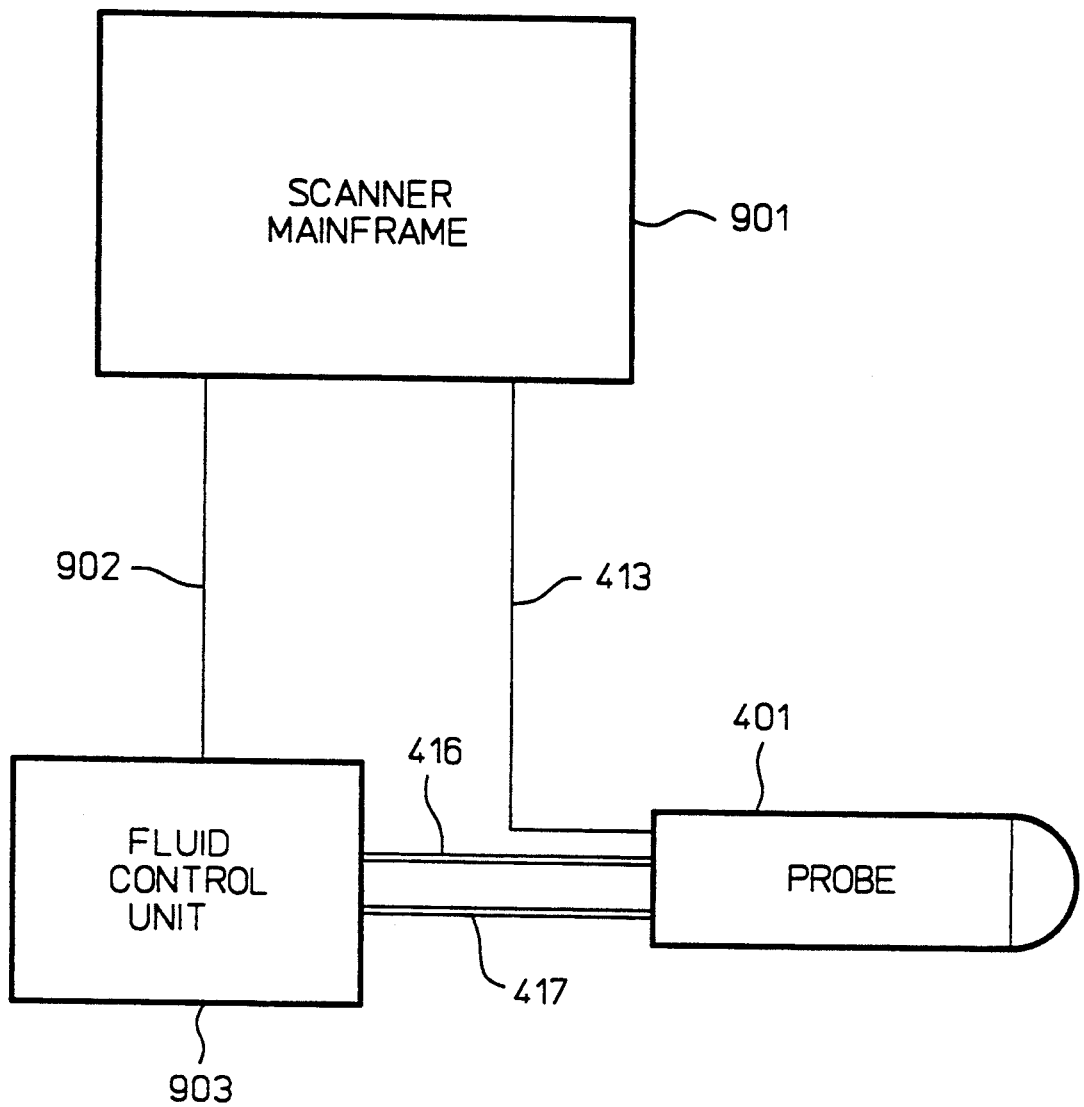
FIG. 9 shows a simplified block diagram of an acoustic imaging system which includes the ultrasound probe shown in FIG. 4, in accordance with a preferred embodiment of the present invention.

FIG. 8 shows a simplified block diagram of a rotation controller/encoder which may be used in any of the previously described ultrasound probes. Turbine rotation 800 is controlled by a ratchet 801. An energy storage spring 802 stores excess energy generated by the turbine. A rotation metering block 803 meters rotation. An angle encoder 804 generates a signal 805 to be returned to a scanner mainframe so that the angular speed of mirror rotation 806 can be obtained. FIG. 9 shows a simplified block diagram of an acoustic imaging system which includes ultrasound probe 401. Fluid control unit 903 controls fluid flow through inflow tube 416 and outflow tube 417. A scanner mainframe 901 generates electrical signals placed on wire cable 413, and processes electrical signals which ultrasound probe 401 places on wire cable 413. The scanner mainframe 901 calculates the angular speed from the frequency of rotation of rotating mirror 402 by decoding the acoustic reflection from the acoustically reflective strip. Scanner mainframe then varies a control signal on control lines 902, to direct fluid control unit 903 to increase or decrease fluid flow so that turbine 405 will rotate at a desired angular speed.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

We claim:

1. An ultrasound probe comprising:
   emission means, located within the ultrasound probe in an ultrasound signal path, the emission means emitting ultrasound signals so that emitted ultrasound signals exit the ultrasound probe; and,
   a turbine, coupled to the emission means, wherein fluid flowing through the turbine causes the turbine to rotate the emission means so that the emitted ultrasound signals sweep an area surrounding the ultrasound probe.

2. An ultrasound probe as in claim 1 wherein the fluid flowing through the turbine is resident within a probed vessel within which the ultrasound probe is situated, the fluid entering the ultrasound probe through holes in a head of the ultrasound probe.

3. An ultrasound probe as in claim 1, additionally comprising:
   fluid vibrating means for vibrating fluid within the ultrasound probe to cause the fluid to pass through the turbine.

4. An ultrasound probe as in claim 3 wherein the fluid vibrating means comprises a piezoelectric transducer.

5. An ultrasound probe as in claim 4 wherein the piezoelectric transducer generates standing acoustic waves within the ultrasound probe.

6. An ultrasound probe as in claim 4 additionally comprising:
   control means, coupled to the turbine, for allowing the turbine to rotate only in a single direction.

7. An ultrasound probe as in claim 3 wherein the fluid vibrating means comprises externally provided fluid transported between the ultrasound probe and an external source via a tube.

8. An ultrasound probe as in claim 7 additionally comprising:
   control means, coupled to the turbine, for allowing the turbine to rotate only in a single direction.

9. An ultrasound probe as in claim 3, wherein the fluid comprises air.

10. An ultrasound probe as in claim 1, additionally comprises:
    fluid provision means for transporting the fluid to the ultrasound probe from an external source.

11. An ultrasound probe as in claim 10 wherein the fluid provision means comprises:
    an inflow tube for transporting the fluid from the external source to the ultrasound probe; and,
    an outflow tube for transporting the fluid from the ultrasound probe to the external source.

12. An ultrasound probe as in claim 1 wherein the ultrasound probe additionally comprises:
    transducing means for generating the ultrasound signals emitted by the emission means.

13. An ultrasound probe as in claim 12 wherein the emission means comprises:
    reflecting means, coupled to the turbine and rotated by the turbine, for reflecting the ultrasound signals generated by the transducing means.

14. An ultrasound probe as in claim 1, additionally comprising:
    an acoustic waveguide which transports the acoustic signals to the emission means;
    wherein the emission means comprises reflecting means, coupled to the turbine and rotated by the turbine, for reflecting the ultrasound signals transported by the acoustic waveguide.

15. An ultrasound probe as in claim 1 wherein the emission means comprises:
    transducing means, coupled to the turbine and rotated by the turbine, for generating the ultrasound signals emitted by the emission means.

16. An ultrasound probe as in claim 1 additionally comprising:
    electrical heating means for generating vapor bubbles in a drive fluid which drive the turbine.

17. A method for providing ultrasound signals which sweep around an ultrasound probe, the method comprising the steps of:
    (a) emitting the ultrasound signals by an emission means so that ultrasound signals exit the ultrasound probe; and,
    (b) driving a turbine, connected to the emission means rotating the emission means, the turbine being driven by fluid flowing through the turbine.

18. A method as in claim 17 wherein step (b) includes providing the fluid from a probed vessel within which the ultrasound probe is situated by allowing the fluid to enter the ultrasound probe through holes in a head of the ultrasound probe.

19. A method as in claim 17 wherein step (b) comprises the substep of:
    (b.1) vibrating fluid within the ultrasound probe to cause the fluid to pass through the turbine.

20. A method as in claim 19 wherein step (b.1) includes vibrating the fluid using a piezoelectric transducer.

21. A method as in claim 19 wherein step (b.1) includes vibrating the fluid using a piezoelectric transducer to produce standing acoustic waves within the ultrasound probe.

22. A method as in claim 19 wherein step (b.1) includes vibrating the fluid using externally provided fluid transported between the ultrasound probe and an external source via a tube.

23. A method as in claim 19 wherein in step (b) the fluid comprises air.

24. A method as in claim 17, wherein step (b) comprises the following substep:
    (b.1) transporting the fluid to the ultrasound probe from an external source.

25. A method as in claim 24 wherein substep (b.1) includes the following substeps:
    transporting the fluid from the external source to the ultrasound probe via an inflow tube; and,
    transporting the fluid from the ultrasound probe to the external source via an outflow tube.

26. A method as in claim 17 additionally comprising the step of:
   (c) generating, within the ultrasound probe, the ultrasound signals emitted by the emission means.

27. A method as in claim 26 wherein step (a) includes: reflecting the ultrasound signals generated with a reflecting surface rotated by the turbine.

28. A method as in claim 17, additionally comprising the step of:
   (c) transporting the acoustic signals to the emission means via an acoustic waveguide;
   wherein step (a) includes reflecting the ultrasound signals transported in step (c) with a reflecting surface rotated by the turbine.

29. A method as in claim 17 wherein step (a) includes: generating the ultrasound signals emitted by the emission means by a transducer which is coupled to the turbine and rotated by the turbine.

30. A method as in claim 17 wherein step (b) includes vaporizing a drive fluid to drive the turbine.

* * * * *